United States Patent [19]

Denis

[11] Patent Number: 5,087,735
[45] Date of Patent: Feb. 11, 1992

[54] PREPARATION OF HEXENEDIOIC ACID DIESTERS

[75] Inventor: Philippe Denis, Decines, France

[73] Assignee: Rhone-Poulenc Chimie, France

[21] Appl. No.: 627,007

[22] Filed: Dec. 13, 1990

[30] Foreign Application Priority Data

Dec. 13, 1989 [FR] France .................. 89 16753

[51] Int. Cl.$^5$ ............................................. C07C 67/38
[52] U.S. Cl. ..................................................... 560/204
[58] Field of Search ......................................... 560/204

[56] References Cited

U.S. PATENT DOCUMENTS

| 3,367,961 | 2/1968 | Brewbaker | 260/532 |
| 4,060,547 | 11/1977 | Paulik et al. | 260/456 |
| 4,575,562 | 3/1986 | Hsu | 560/204 |
| 4,633,015 | 12/1986 | Chan et al. | 560/590 |
| 4,857,657 | 8/1989 | Denis et al. | 560/204 |
| 4,925,973 | 5/1990 | Deweerdt | 560/204 |

FOREIGN PATENT DOCUMENTS 272191 10/1987 European Pat. Off. .

Primary Examiner—Paul J. Killos

[57] ABSTRACT

Hexenedioic acid diesters, e.g., a hex-3-ene-1,6-dioic acid diester, are prepared by reacting carbon monoxide and an alcohol with at least one diacyloxylated butene in a polar, aprotic, basic solvent, in the presence of a catalytically effective amount of palladium values and at least one inorganic halide, the cation of which halide being an alkali or alkaline earth metal and the anion thereof being a chloride or bromide.

14 Claims, No Drawings

PREPARATION OF HEXENEDIOIC ACID DIESTERS

CROSS-REFERENCE TO COMPANION APPLICATIONS

Copending application Ser. No. 07/626833 filed 13 Dec. 1990 and Serial No. 07/626774 filed Dec. 13, 1990, both filed concurrently herewith and both assigned to the assignee hereof.

BACKGROUND OF THE INVENTION

1. Field of the Invention

The present invention relates to an improved process for the preparation of hexene-1,6-dioic acid diesters. Such diesters are valuable intermediates that can facilely be hydrogenated into corresponding adipic acid diesters or adipates, which can then be hydrolyzed into adipic acid.

2. Description of the Prior Art

Adipic acid, one of the starting materials for the production of nylon 66, is produced in vast amounts per annum. By reason of this fact alone, any new route for the synthesis of this diacid and/or derivatives thereof would be of fundamental interest to this art.

The preparation of a monoester of an alcohol and a butenoic acid by reacting carbon monoxide and an alcohol with an allyl alcohol monoester in the present of a palladium-based catalyst is described in U.S. Pat. No. 3,367,961. Thus, ethyl vinylacetate can be prepared from allyl acetate, carbon monoxide and ethanol in the presence of palladium chloride and palladium deposited on charcoal.

U.S. Pat. No. 4,611,082 indicates that the carbonylation of a solution of 1,4-diacetoxybut-2-ene in a aprotic, polar and non-basic solvent selected from among the nitriles, bis(2-methoxy)but-2-ene, bis(2-methoxyethyl) ether and methylene chloride, at 80° to 140° C., in the presence of a transition metal halide is virtually absent, and that, in the presence of an alcohol, the extent of carbonylation increases and is comparable to that observed for the carbonylation of but-2-ene-1,4-diol. With regard to this latter substrate, it is also indicated that satisfactory yields of straight-chain carbonylation compounds are not obtained under the above conditions. Thus, the preferred substrates are substituted in the 1,4-position by alkoxy groups.

As 1,4-diacetoxybut-2-ene is readily produced by acetoxylation of butadiene, a valuable addition to this art would be a process for preparing hex-3-ene-1,6-dioic acid diesters, in high efficiency, from 1,4-diacetoxybut-2-ene, in particular, and more generally from butenes disubstituted by acyloxy groups.

Published European Application No. 89/4,201,995 describes a process for the preparation of hex-3-ene dioic acid diesters by reacting carbon monoxide and an alcohol with at least one butene disubstituted by acyloxy groups in the presence of a palladium-based catalyst and a quaternary onium halide of a Group VB element of the Periodic Table selected from nitrogen and phosphorus, such element being tetracoordinated to carbon atoms, with the proviso that the nitrogen may be coordinated to two pentavalent phosphorus atoms, and the halide anion being a chloride or bromide.

The process of the '995 application, which provides appreciable results both in respect of its activity and in respect of its selectivity for a straight-chain dicarbonylated compound, however, presents the disadvantage or requiring the presence of at least one quaternary onium halide as indicated above. These onium compounds are promoters which are relatively expensive or not readily available and are susceptible to degradation over prolonged use.

Thus, need exists in this art for an alternate process that does not require a halogenated organic promoter, and particularly one wherein all or part of such organic promoter may be replaced by an inorganic halogenated promoter which is more readily available and relatively more stable over prolonged use.

SUMMARY OF THE INVENTION

Accordingly, a major object of the present invention is the provision of an improved process for the preparation of hex-3-enedioic acid diesters, by reacting carbon monoxide and an alcohol with at least one butene disubstituted by acyloxy groups in the presence of a palladium-based catalyst and a halide, such reaction being carried out in a polar, aprotic, basic solvent and in the presence of at least one inorganic halide, the cation of which is an alkali metal or an alkaline earth metal cation, and the anion of which is a chloride or bromide.

DETAILED DESCRIPTION OF THE PREFERRED EMBODIMENTS OF THE INVENTION

More particularly according to the present invention, it has now surprisingly been found that the subject process permits the dicarbonylation to be carried out under conditions of pressure and temperature which are acceptable on an industrial scale, with an appreciable selectivity for straight-chain dicarbonylated compounds, the proportions of monocarbonylated compounds and branched dicarbonylated compounds being minimal.

The process of this invention can be represented by the following reaction scheme when the starting materials include a but-2-ene disubstituted in the 1,4-position by acyloxy groups:

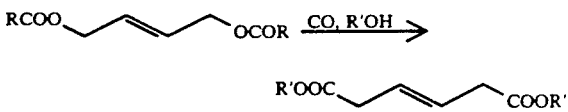

in which R is a straight or branched chain alkyl radical having from 1 to 12 carbon atoms, optionally substituted by a phenyl radical, or an aryl radical having from 6 to 10 carbon atoms, optionally substituted by one or two alkyl radicals having from 1 to 4 carbon atoms; or a substituted such radical containing from 1 to 3 substituents selected from among fluorine and chlorine atoms and dialkylamino and N,N-dialkylamido radicals in which the alkyl moieties have up to 4 carbon atoms; and R', which is identical to or different from R, is a straight or branched chain alkyl radical having from 1 to 12 carbon atoms, optionally substituted by a phenyl radical, or an aryl radical having from 6 to 10 carbon atoms, optionally substituted by one or two alkyl radicals having from 1 to 4 carbon atoms; or a substituted such radical containing from 1 to 3 substituents selected from among fluorine, bromine and chlorine atoms.

The process according to the present invention requires at least one butene disubstituted by acyloxy groups. By "acyloxy group" are intended radicals of the formula RCOO—, in which R is as defined above; by "disubstituted butenes" are intended the but-2-ene compounds substituted in the 1- and 4-positions and the but-1-ene compounds substituted in the 3- and 4-positions. Of course, mixtures of but-2-ene disubstituted by acyloxy groups of different nature, mixtures of but-1-ene disubstituted by acyloxy groups of different nature or mixtures of disubstituted but-2-ene and but-1-ene may also be used in the process of the invention.

Indeed, it has now been found that the selectivity for a straight-chain diester is substantially the same whether a but-2-ene disubstituted by acyloxy groups in the 1,4-position or a but-1-ene disubstituted by acyloxy groups in the 3- and 4-positions is used as a starting material.

Exemplary butenes disubstituted by acyloxy groups include diacetoxybutenes, dipropionyloxybutenes, dibutyryloxybutenes and dibenzoyloxybutenes.

1,4-Diacetoxybut-2-ene, 3,4-diacetoxybut-1-ene and mixtures thereof are more particularly preferred for carrying out the process of the present invention.

The process of this invention also requires the use of an alcohol of the formula R'OH, in which R' is as defined above.

Exemplary such alcohols include: methanol, ethanol, isopropanol, n-propanol, tert-butanol, n-hexanol, 2-ethylhexanol, nonan-1-ol, dodecanol, phenylethanol, phenol and trifluoroethanol.

An alkanol in which the radical R' has at most 12 carbon atoms, and preferably 4 carbon atoms, is advantageously used.

The amount of alkanol to be used is not critical and may vary over wide limits.

Nonetheless, good results are obtained using a molar ratio of alcohol to disubstituted butene ranging from 1 to 100 and preferably from 1 to 50.

The process according to the invention is also carried out in the presence of a palladium-based catalyst.

While the precise nature of the mechanism of such catalysis is not totally understood, it has been found that a very wide variety of palladium compounds and metallic palladium are useful catalysts, or precursors thereof, for carrying out the process of the present invention.

Exemplary sources of palladium which may thus be used include the following:

(i) metallic palladium, if appropriate deposited onto a support therefor, such as charcoal, alumina or silica;

(ii) $PdCl_2$, $Pd(OAc)_2$;

(iii) the salts or $\pi$-allyl complexes of palladium, in which the anion coordinated to the Pd cation is selected from among the following anions: carboxylates, such as formate, acetate, propionate or benzoate; acetylacetonate and halides such as $Cl^-$ and $Br^-$, and preferably $Cl^-$.

Advantageously, palladium chloride is used.

The precise amount of catalyst to be used, which may vary over wide limits, will primarily depend on all compromise between the desired efficiency and the consumption of catalyst and the other reaction conditions. In general, good results are obtained using a palladium concentration in the reaction mixture ranging from $10^{-3}$ to one mol/l. Preferably, this concentration ranges from $2 \cdot 10^{-3}$ to $5 \cdot 10^{-2}$ mol/l.

One of the essential characteristics of the process of the present invention is that the reaction is carried out in a polar, aprotic and basic solvent.

By "polar, aprotic and basic solvent" are especially intended compounds of the formula (I):

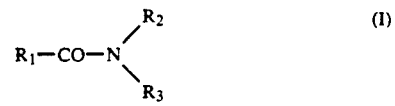

in which $R_1$, $R_2$ and $R_3$, which may be identical or different, are each an alkyl radical, a cycloalkyl radical, an aralkyl radical or a monocyclic aryl radical having up to 10 carbon atoms, with the proviso that two of the radicals $R_1$, $R_2$ and $R_3$ may together form a single divalent radical —$(CH_2)_y$—, in which y is an integer ranging from 3 to 12, and further wherein $R_1$ may be a radical of the formula (II):

in which $R_4$ and $R_5$, which may be identical or different, are each an alkyl radical having up to 4 carbon atoms.

Exemplary such solvents include tetramethylurea, N,N-dimethylacetamide, N,N-diethylacetamide, N,N-dicyclohexylacetamide, N,N-dimethylpropionamide, N,N-diethylpropionamide, N,N-diethyl-n-butyramide, N,N-dimethylbenzamide, N,N-dicyclohexylbenzamide, N,N-diethyl-m-toluamide, N-acetylpyrrolidine, N-acetylpiperidine, N-(n-butyryl)-piperidine, N-methylpyrrolid-2-one, N-ethylpyrrolid-2-one, N-methylpiperid-2-one, N-methyl-epsilon-caprolactam.

N-Methylpyrrolid-2-one is particularly suitable for carrying out the subject process.

In general, the amount of solvent constitutes at least 10% by volume of the reaction mixture; good results are obtained when it is used in an amount on the order of 20% to 85% by volume.

Another characteristic of the process according to the invention is that the reaction is also carried out in the presence of a halide, the cation of which is selected from among the alkali metal cations and the alkaline earth metal cations, the halide anion being selected from the chloride and bromide.

Exemplary such halides include LiCl, LiBr and $CaCl_2$.

It has also been determined that the beneficial effect provided by the presence of an alkali metal chloride or bromide or alkaline earth metal chloride or bromide in the carbonylation mixture is perceptible from a molar ratio $Cl^-$ (or $Br^-$)/palladium of 0.5; in particular, particularly desirable results are obtained when said ratio ranges from 1 to 50, a higher ratio, however, not being detrimental to the reaction.

Of course, a mixture of such inorganic halides or a mixture thereof with at least one quaternary onium halide as defined above can also be employed according to the present invention.

The reaction is advantageously carried out in liquid phase at a temperature ranging from 50° to 150° C., preferably from 80° to 130° C., under a carbon monoxide pressure ranging from 20 to 250 bar, preferably from 90 to 180 bar.

Inert gases, such as nitrogen, argon or carbon dioxide, may also be present together with the carbon monoxide.

Upon completion of the reaction or at the end of predetermined reaction time, the desired diester is recovered by any appropriate means, for example, by extraction and/or distillation.

In order to further illustrate the present invention and the advantages thereof, the following specific examples are given, it being understood that same are intended only as illustrative and in nowise limitative.

In said examples to follow, the yields are expressed relative to diacetoxybutene charged.

EXAMPLES 1 TO 5

Control Experiments (a) to (d)

The following reagents were introduced into a 125 cm³ stainless steel (Hastelloy B2) autoclave previously purged with argon:

(i) 4.3 g (25 mmol) of 1,4-diacetoxybut-2-ene;
(ii) methanol;
(iii) 1 mat-g of palladium in the form of $PdCl_2$;
(iv) if necessary, 17 mmol of calcium chloride (lithium chloride or lithium bromide);
(v) N-methylpyrrolid-2-one (NMP) or, if necessary, another solvent.

The autoclave was hermetically sealed, placed in a stirred furnace and connected to the pressurized gas feed. The reactor was purged cold with carbon monoxide and adjusted to 100° C. The pressure was then adjusted to 120 bar. When the absorption of carbon monoxide had ceased, the autoclave was cooled and degassed.

The reaction mixture was then esterified using methanol and then analyzed by gas phase chromatography.

The particular conditions and the results obtained are reported in the Table below, in which t(min) represents the absorption period and HD(%) represents the molar amount of methyl hex-3-enedioate formed per 100 moles of 1,4diacetoxybutene charged.

The degree of conversion of the 1,4diacetoxybutene was on the order of 100% in all of the experiments.

TABLE:

| Example | Nature of the halide | MeOH | NMP | t (min) | HD (%) |
|---|---|---|---|---|---|
| 1 | none | 53 mmol | 20 cm³ | 390 | 53.5 |
| a (*) | LiI | 53 mmol | 20 cm³ | 180 | 0 |
| 2 | LiBr | 53 mmol | 20 cm³ | 120 | 76 |
| 3 | LiCl | 53 mmol | 20 cm³ | 90 | 95 |
| 4 | $CaCl_2$ | 53 mmol | 20 cm³ | 60 | 95 |
| 5 | $CaCl_2$ | 10 cm³ | 10 cm³ | 50 | 72.5 |
| b | $CaCl_2$ | 20 cm³ | 0 | 120 | 0 |
| c (*) | $CaCl_2$ | 0 | 20 cm³ | 120 | 0 |
| d | LiCl | 10 cm³ | toluene 10 cm³ | 60 | 26 |

(*) In these experiments, the presence, on the order of 30% to 40% of methyl pentadienoate, was detected.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a hex-3enedioic acid diester, comprising reacting carbon monoxide and an alcohol with at least one diacyloxylated butene in a polar, aprotic, basic solvent, in the presence of a catalytically effective amount of palladium values, and at least one inorganic halide, the cation of which comprising an alkali or alkaline earth metal and the anion thereof comprising a chloride or bromide.

2. The process as defined by claim 1, said solvent comprising a compound of the formula (I):

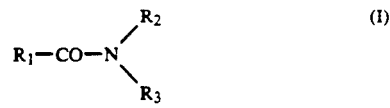

in which $R_1$, $R_2$ and $R_3$, which may be identical or different, are each an alkyl radical, a cycloalkyl radical, an aralkyl radical or a monocyclic aryl radical having up to 10 carbon atoms, with the proviso that two of the radicals $R_1$, $R_2$ or $R_3$, may together form a single divalent radical $-(CH_2)_y-$, wherein y is an integer ranging from 3 to 12, and further wherein $R_1$ may be a radical of the formula (II):

in which $R_4$ and $R_5$, which may be identical or different, are each an alkyl radical having up to 4 carbon atoms.

3. The process as defined by claim 1, wherein said solvent comprises at least 10% by volume of the reaction mixture.

4. The process as defined by claim 1, said solvent comprising N-methylpyrrolid-2-one.

5. The process as defined by claim 1, wherein the molar ratio of the chloride or bromide anion to palladium ranges from 1 to 50.

6. The process as defined by claim 1, wherein the amount of palladium in the reaction mixture ranges from $10^{-3}$ to 1 mol/l.

7. The process as defined by claim 1, wherein the molar ratio of the alcohol to the disubstituted butene ranges from 1 to 100.

8. The process as defined by claim 1, carried out at a reaction temperature ranging from 50° to 150° C.

9. The process as defined by claim 8, carried out at a pressure ranging from 20 to 250 bar.

10. The process as defined by claim 1, said disubstituted butene comprising 1,4-diacetoxybut-2-ene, 3,4-diacetoxybut-1-ene or mixture thereof.

11. The process as defined by claim 1, said palladium values comprising palladium chloride.

12. The process as defined by claim 7, said molar ratio ranging from 1 to 50.

13. The process as defined by claim 8, said reaction temperature ranging from 80° to 130° C.

14. The process as defined by claim 9, said pressure ranging from 90 to 180 bar.

* * * * *